(12) United States Patent
Vinciguerra et al.

(10) Patent No.: US 7,278,989 B2
(45) Date of Patent: Oct. 9, 2007

(54) METHOD FOR ANALYSIS OF AN ABLATED SURFACE, ANALYSIS ON INCONSISTENCY IN A LASER BEAM, AND CALIBRATION OF LASER BEAM IRRADIATION DATA

(75) Inventors: Paolo Vinciguerra, Milan (IT); Hiroyuki Hiramatsu, Hoi-gun (JP); Yoshitaka Suzuki, Okazaki (JP)

(73) Assignee: Nidek Co. Ltd. (JP)

( * ) Notice: Subject to any disclaimer, the term of this patent is extended or adjusted under 35 U.S.C. 154(b) by 381 days.

(21) Appl. No.: 10/511,897

(22) PCT Filed: Apr. 30, 2002

(86) PCT No.: PCT/JP02/04344

§ 371 (c)(1),
(2), (4) Date: Oct. 20, 2004

(87) PCT Pub. No.: WO03/092565

PCT Pub. Date: Nov. 13, 2003

(65) Prior Publication Data

US 2005/0143716 A1    Jun. 30, 2005

(51) Int. Cl.
*A61B 18/20* (2006.01)
(52) U.S. Cl. .................. 606/5; 606/4; 128/898
(58) Field of Classification Search ........... 606/4–6, 606/10–12; 351/205, 212; 128/898
See application file for complete search history.

(56) References Cited

U.S. PATENT DOCUMENTS

| 5,624,436 A | * | 4/1997 | Nakamura et al. ............ 606/12 |
| 5,637,109 A | | 6/1997 | Sumiya |
| 5,906,608 A | | 5/1999 | Sumiya et al. |
| 5,907,388 A | | 5/1999 | Fujieda |
| 6,033,075 A | * | 3/2000 | Fujieda et al. .............. 351/212 |
| 6,245,058 B1 | * | 6/2001 | Suzuki ......................... 606/2 |
| 6,607,521 B2 | * | 8/2003 | Vinciguerra et al. ........... 606/5 |
| 6,932,806 B2 | * | 8/2005 | Nakamura .................... 606/5 |
| 6,994,701 B2 | * | 2/2006 | Okamoto et al. .............. 606/5 |

FOREIGN PATENT DOCUMENTS

| EP | 0 947 158 A1 | 10/1999 |
| JP | 06-114083 | 4/1994 |
| JP | 6-226471 A | 8/1994 |
| JP | 09-266925 | 10/1997 |
| JP | 10-108837 | 4/1998 |
| JP | 11-342152 A | 12/1999 |
| JP | 2002-065719 A | 3/2002 |

OTHER PUBLICATIONS

International Search Report dated Aug. 20, 2002.

* cited by examiner

*Primary Examiner*—A. Farah
(74) *Attorney, Agent, or Firm*—Rader Fishman & Grauer PLLC; Ronald P. Kananen

(57) ABSTRACT

A method and an apparatus for evaluating ablation conditions easily and for ablating a target object accurately. The method includes irradiating a reference object with a laser beam under laser irradiation conditions determined to form a second curved surface shape on the reference object having a first curved surface shape approximate to a curved surface shape of the target object, measuring a third curved shape which has actually been formed by the laser irradiation, and determining a discrepancy between the second and the third curved surface shapes. Then, data about ablation or data for controlling a laser irradiation apparatus are corrected based on results of the determination.

3 Claims, 6 Drawing Sheets

METHOD FOR ANALYSIS OF AN ABLATED SURFACE, ANALYSIS ON INCONSISTENCY IN A LASER BEAM, AND CALIBRATION OF LASER BEAM IRRADIATION DATA

BACKGROUND OF THE INVENTION

1. Field of the Invention

The present invention relates to a method for ablating a target object with a laser beam and an apparatus for such ablation.

2. Description of Related Art

A laser beam is used in various fields for medical treatment or processing. For example, in the ophthalmic field, there have been known laser apparatuses for ablating a cornea with a laser beam to change its corneal curvature so that a refractive error of an eye may be corrected. In this type of apparatus, an ablation rate (an ablation depth) per one shot of laser beams (or per one scan) often changes due to factors including laser output and changes in an irradiating optical system (a beam directing optical system). Therefore, it is important to ablate a target object such as a cornea in consideration of the change of the ablation rate.

The present applicant suggested a method for adapting to the change of the ablation rate in Japanese Patent Application Unexamined Publication No. Hei 06-226471 which corresponds to U.S. Pat. No. 5,624,436. The method consists of performing laser irradiation to ablate a surface of a transparent plate (a PMMA plate) having a known ablation rate so that the ablated surface may have a curved surface shape and intended refractive power, measuring with a lens meter or the like the refractive power of the curved surface of the transparent plate formed by the ablation, and correcting data for intended ablation based on a result of the measurement.

Such a method has provided a way to ablate a target object in consideration of the change of the ablation rate. Meanwhile, further techniques for more accurate ablation have been explored.

The present invention has been made in view of the above circumstances and has an object to overcome the above problems and to provide a method for easily evaluating ablation conditions and accurately ablating a target object, as well as an apparatus for such ablation.

DISCLOSURE OF THE INVENTION

To achieve the objects and in accordance with the purpose of the present invention, as embodied and broadly described herein, the present invention has the following features.

1) A method for ablating a target object with a laser beam has an irradiation step of irradiating a reference object having a first curved surface shape with the laser beam under laser irradiation conditions determined to form a second curved surface shape on the reference object, where the first curved surface shape is approximate to a curved surface shape of the target object, a measurement step of measuring a third curved surface shape actually formed by the laser irradiation, and an analysis step of determining a discrepancy between the second curved surface shape and the third curved surface shape.

2) The ablation method further has a correction step of correcting control data for a laser irradiation apparatus based on a result of the analysis.

3) The ablation method further has an input step of inputting ablation data for changing the curved surface shape of the object into a desired surface shape and a correction step of correcting the inputted ablation data based on a result of the analysis.

4) The ablation method further has a display step of displaying a result of the analysis.

5) In the ablation method, the target object includes a cornea, and an apparatus for corneal shape measurement is used in the measurement step.

6) In addition, in the ablation method, the reference object has a known ablation rate relative to an ablation rate of the target object.

7) An apparatus for ablation has measurement data input means for inputting data obtained by irradiating a reference object having a first curved surface shape with a laser beam under laser irradiation conditions determined to form a second curved surface shape on the reference object and by measuring a third curved surface shape on the reference object actually formed by the laser irradiation, wherein the first curved surface shape is approximate to a curved surface shape of a target object, and analysis means for determining a discrepancy between the second curved surface shape and the third curved surface shape.

8) The apparatus for ablation includes a laser irradiation apparatus provided with an irradiating optical system for irradiating the object with the laser beam, and control means for controlling an irradiation position and irradiation time of the laser beam emitted by the irradiating optical system, and the apparatus further has correction means for correcting control data for the control means based on a result of the analysis.

9) Furthermore, the apparatus for ablation has ablation data input means for inputting ablation data for changing the curved surface shape of the target object into a desired surface shape, and correction means for correcting the inputted ablation data, based on the analytical result.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

BEST MODE FOR CARRYING OUT THE INVENTION

Figure 1:
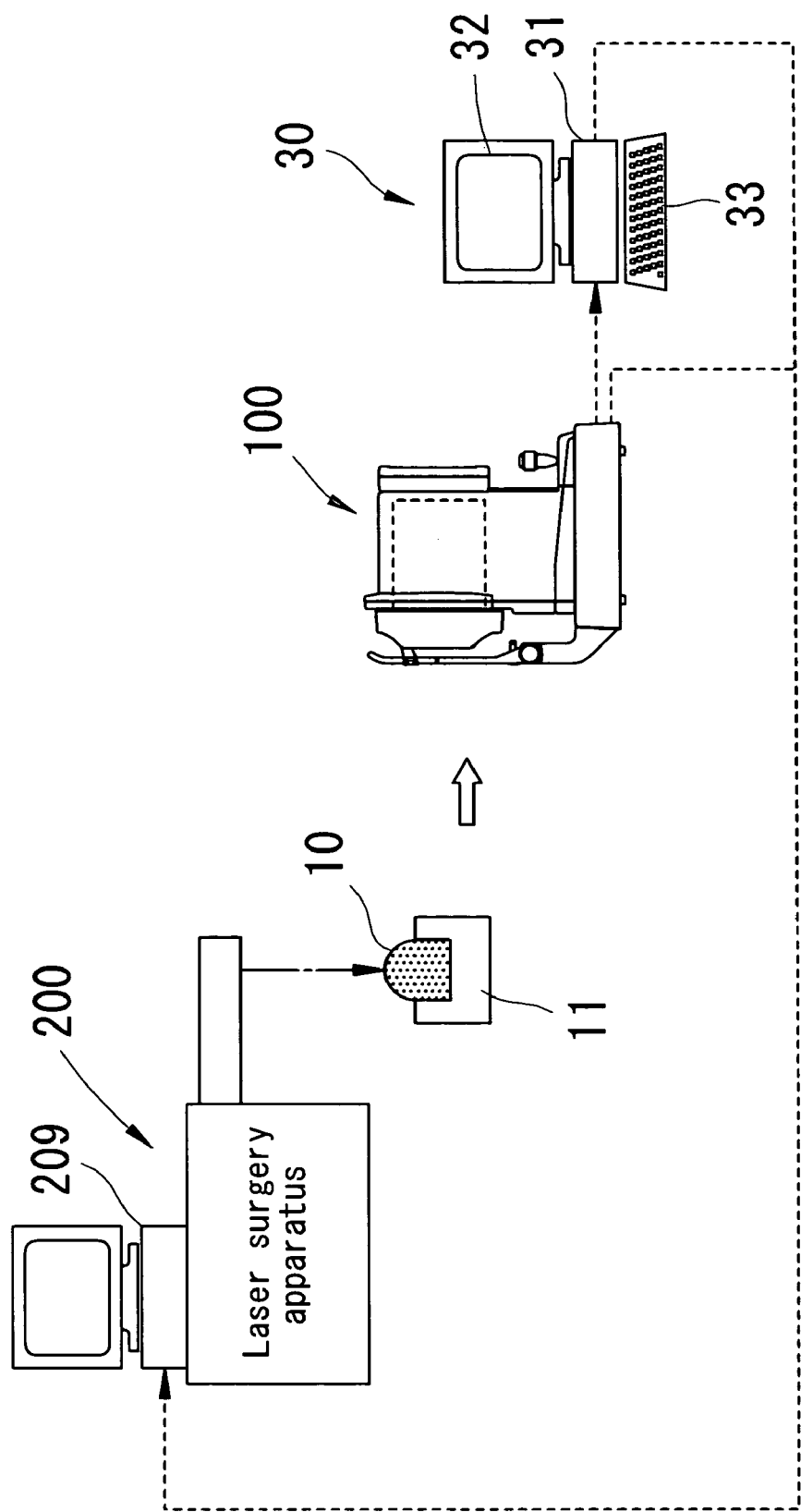
FIG. 1 is a view showing a schematic configuration of an ablation system.

A detailed description of one preferred embodiment of the present invention will now be given referring to the accompanying drawings. FIG. 1 is a view showing a schematic configuration of an ophthalmic ablation system.

A laser irradiation apparatus 200 ablates a cornea of a patient's eye with a laser beam. A reference object 10 has a convex curved surface shape, and is used for calibrating the irradiation apparatus 200. The reference object 10 is made of transparent polymethyl methacrylate (PMMA), and its convex curved surface shape is similar to a corneal shape of a human eye in view of curvature. For example, the reference object 10 has a hemispherical surface with a radius of curvature R of 7.8 mm being the average for a human eye. The hemispherical surface has a diameter of 12 mm, and it is preferred that the diameter be more than 10 mm. A supporter 11 supports the reference object 10, and the supporter 11 may have any configuration as long as it is capable of supporting the reference object 10 stably during laser irradiation. It is preferred to provide dusting means (e.g. a fan for blowing off cuttings or a suction pump for sucking cuttings) near the supporter 11 or the reference object 10 so that the cuttings produced by the laser irradiation may be prevented from adhering to a surface to be ablated and from affecting the shape of the ablated object.

As will be described later, a corneal shape measurement apparatus 100 projects a plurality of annular placido rings onto a cornea of a patient's eye, and detects images of those rings to obtain a corneal curvature distribution over a large part of the cornea, thereby measuring a surface shape of the cornea. It should be noted that the corneal shape measurement is not limited to a configuration in which the placid rings are used, and the measurement apparatus may be configured such that slit light may section the cornea to obtain its cross-sectional image for measuring a surface shape of the cornea. In addition, the measurement apparatus 100 is also used for measuring a shape of the reference object 10, not only the shape of the cornea. This eliminates a need to prepare another apparatus particularly for measuring the reference object 10, which is economically advantageous.

An analyzer 30 has an analysis part 31, a monitor 32, and an input part 32 such as a keyboard. The analysis part 31 has a capability of determining (analyzing) ablation data for refractive surgery based on data about the corneal shape and data about the distribution of eye refractive power, both sets of data being obtained from the measurement apparatus 100. In addition, the analysis part 31 also has a capability of determining (analyzing) discrepancy by ablation and the like based on the measurement result of the reference object 10, a capability of determining (analyzing) data for calibrating the irradiation apparatus 200, and the like. The analytical results obtained by the analyzer 30 are inputted to a computer 209 of the irradiation apparatus 200. Incidentally, instead of the analyzer 30, the measurement apparatus 100 or the computer 209 may be configured to have those capabilities.

Figure 2:
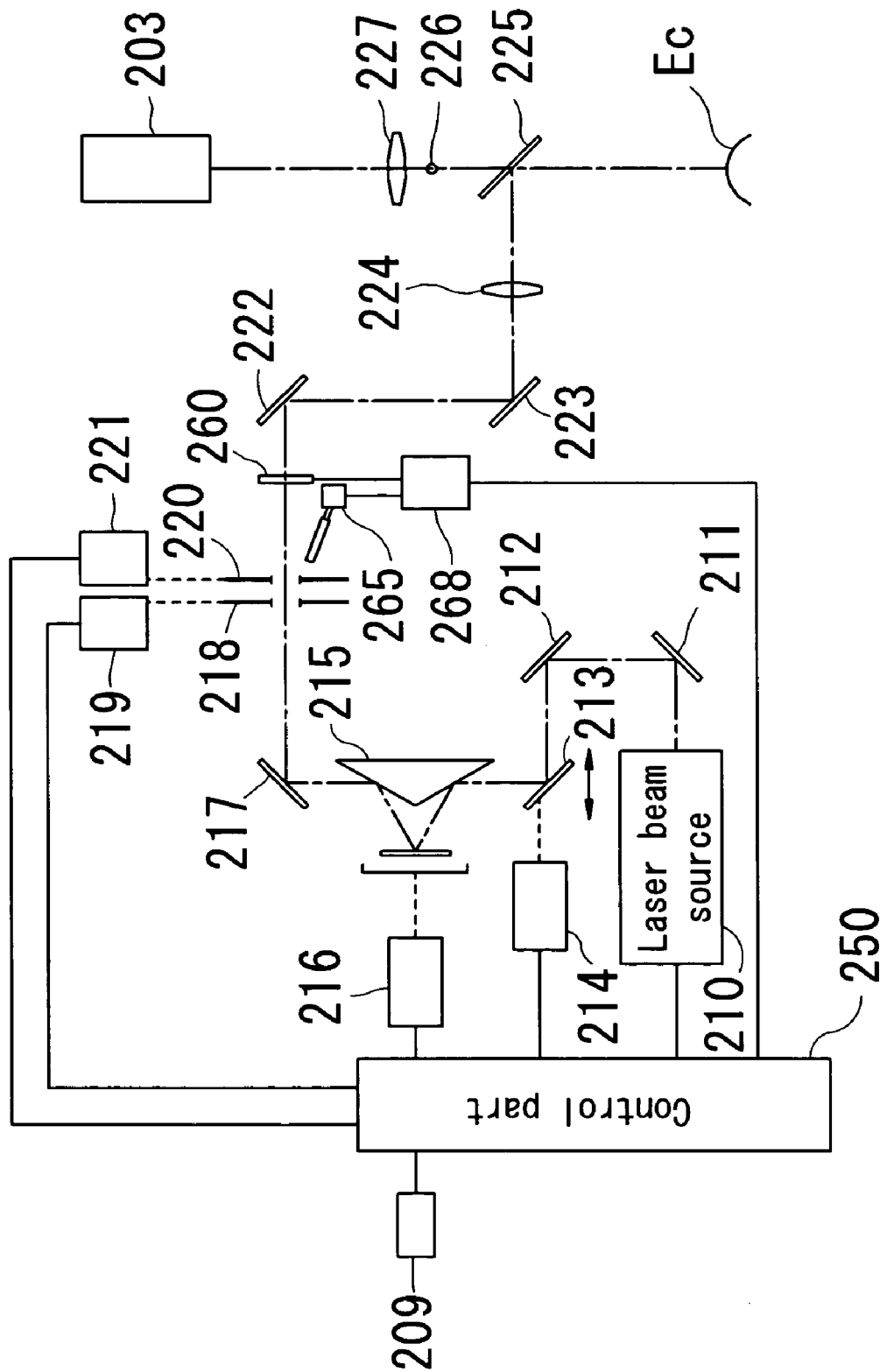
FIG. 2 is a view showing a schematic configuration of an irradiating optical system and a control system in a laser irradiation apparatus.

FIG. 2 is a view illustrating a schematic configuration of an irradiating optical system (a beam directing optical system) and a control system in the irradiation apparatus 200. A laser beam source 210 emits an excimer laser beam with a wavelength of 193 nm. The laser beam emitted from the laser beam source 210 is reflected by mirrors 211 and 212, and is further reflected by a plane mirror 213. A mirror-driving part 214 allows the mirror 213 to move (translate) in a direction of an arrow in the figure, and the mirror 213 thereby shifts (moves) the laser beam (i.e. performs scanning) in parallel to the Gaussian distribution. An image-rotator driving part 216 drives an image rotator 215 rotatably about a central optical axis, and the image rotator 215 thereby rotates the laser beam about the central optical axis. A mirror 217 reflects the laser beam.

A variable circular aperture 218 confines an ablation zone to a circular shape, and an aperture-driving part 219 varies an opening diameter of the aperture 218. A variable slit aperture 220 confines the ablation zone to a slit shape, and an aperture-driving part 221 varies an opening width and a slit direction of the aperture 220. Mirrors 222 and 223 reflects the laser beam. A projecting lens 224 projects the circular aperture 218 and the slit aperture 220 onto a cornea Ec of a patient's eye.

Figure 3:
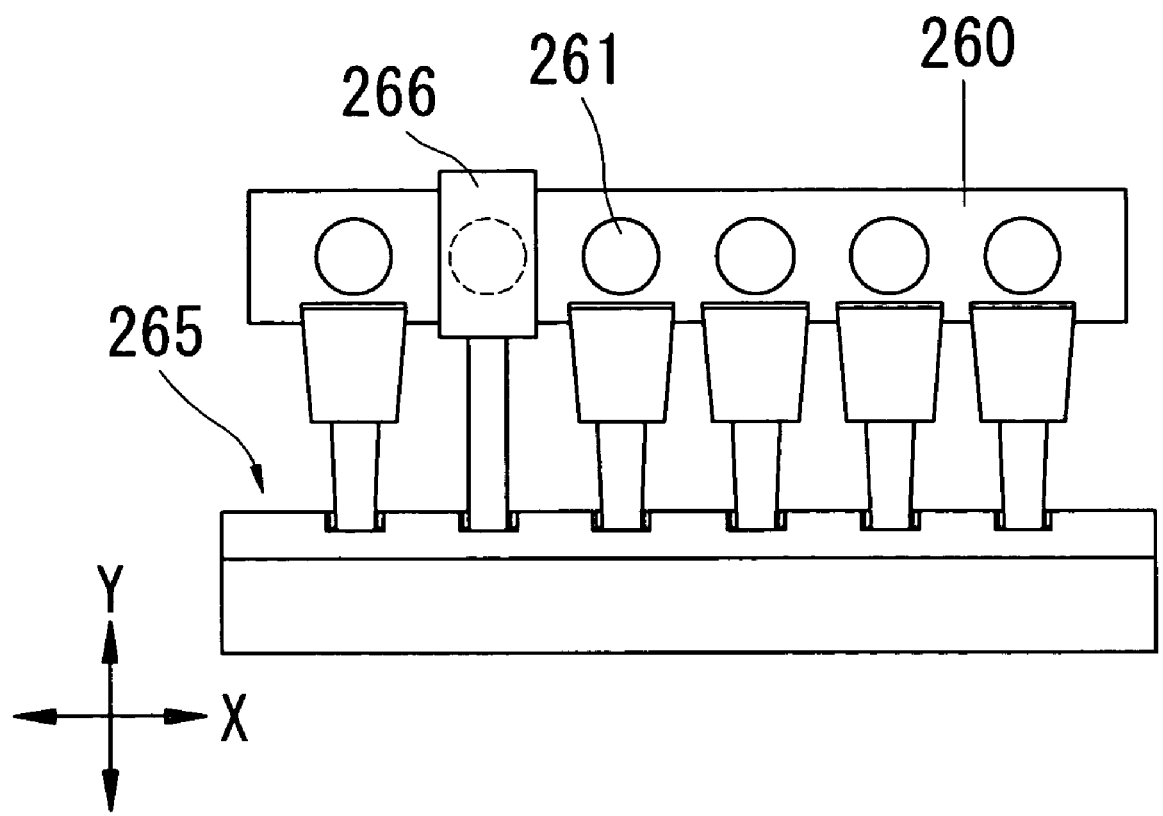
FIG. 3 is a view showing a schematic configuration of a dividing aperture plate.

In addition, a dividing aperture plate 260 is placed in an optical path between the slit aperture 220 and the mirror 222 so that the plate 260 may be inserted into and removed from the optical path. The dividing aperture plate 260 operates in concert with a dividing shutter 265 to confine the ablation zone further; in other words, the plate 260 in combination with the shutter(s) 265 selectively extracts a zone to be scanned (irradiated). The plate 260 and the shutter 265 are used to ablate an asymmetrical component of the cornea Ec. When the plate 260 is viewed from the side of the beam source 210, there are six circular small apertures 261 of one size to be seen in a row as shown in FIG. 3. One or more of the small apertures 261 are selectively covered and uncovered by shutter plates 266 included in the shutter 265. Thus, laser irradiation may be performed while the ablation zone is further confined. Each of the small apertures 261 is provided with a correction optical system for correcting a laser beam intensity distribution caused by diffraction occurring when the laser beams pass through those apertures. A driving part 268 moves the plate 260 and the shutter 265 within a plane perpendicular to the central optical axis.

A dichroic mirror 225 has a property of reflecting the excimer laser beam of 193 nm and transmitting visible light and infrared light. The dichroic mirror 225 reflects the laser beam having passed through the projecting lens 224, whereby the laser beam is irradiated on (directed to) the cornea Ec. Placed above the dichroic mirror 225 are a fixation light 226, an objective lens 227, and a binocular microscope part 203.

A control part 250 controls the laser beam source 210, the driving parts 214, 216, 219, 221, 268 and the like, and connects to the computer 209.

In the irradiation apparatus 200, ablation is performed as will be described below. For performing ablation to a constant depth, the mirror 213 is moved in the direction of the arrow in FIG. 2 to provide a scan with the laser beam in the Gaussian distribution at a speed corresponding to a repetition frequency of laser pulses from the laser beam source 210. The mirror 213 is moved in synchronization with the laser pulses. That is, the mirror 213 is moved from one position to the next position after one or more laser pulses are emitted, and the mirror 213 is moved again after one or more subsequent laser pulses are further emitted. This operation is repeated across the zone confined by the opening of the aperture 218. Besides, the scanning direction is shifted by a predetermined angle after each scan. Preferably, the scanning directions are spread out in a radial form. It should be noted that the method of ablating an object uniformly is described in detail in Japanese Patent Application Unexamined Publication No. Hei 06-114083 corresponding to U.S. Pat. No. 5,637,109, which is to be referred to for more information.

Further, a moving speed of the mirror 213 may be varied during one scan to make variations in how the laser pulses overlap one another on the target object. Therefore, a surface of the object, even if it is convex and curved, may be ablated to an approximately uniform depth under appropriate control of the moving speed of the mirror 213.

When a spherical component for myopic correction is to be removed by ablating a central part of the cornea Ec deeply, the following steps are carried out. First, the mirror 213 is moved sequentially to provide scans with the laser beam in the Gaussian distribution within the zone confined by the opening of the aperture 218. Then the scanning direction of the laser beam is shifted by the rotation of the image rotator 215 each time the laser beam complete one scan (e.g. the scanning is performed in three directions spaced at 120 degrees.) This operation is repeated each time the opening diameter of the circular aperture 218 is changed in sequence, thereby ablating the central part of the cornea Ec deeply and its peripheral part shallowly. For removing an astigmatic component, instead of the circular aperture 218, the slit aperture 220 is used to control the ablation zone and the ablation depth in the same manner.

Furthermore, the dividing aperture plate 260 is used for partial ablation. The dividing aperture plate 260 is placed in the optical path, and the positions of the small apertures 261 included in the plate 260 are controlled while one or more of the small apertures 261 are selectively covered and uncovered by the dividing shutter 265. When the mirror 213 moves to provide the scan with the laser beam, the laser beam passes through only those uncovered of the small apertures 261, so that the laser beam is partially irradiated.

Figure 4:
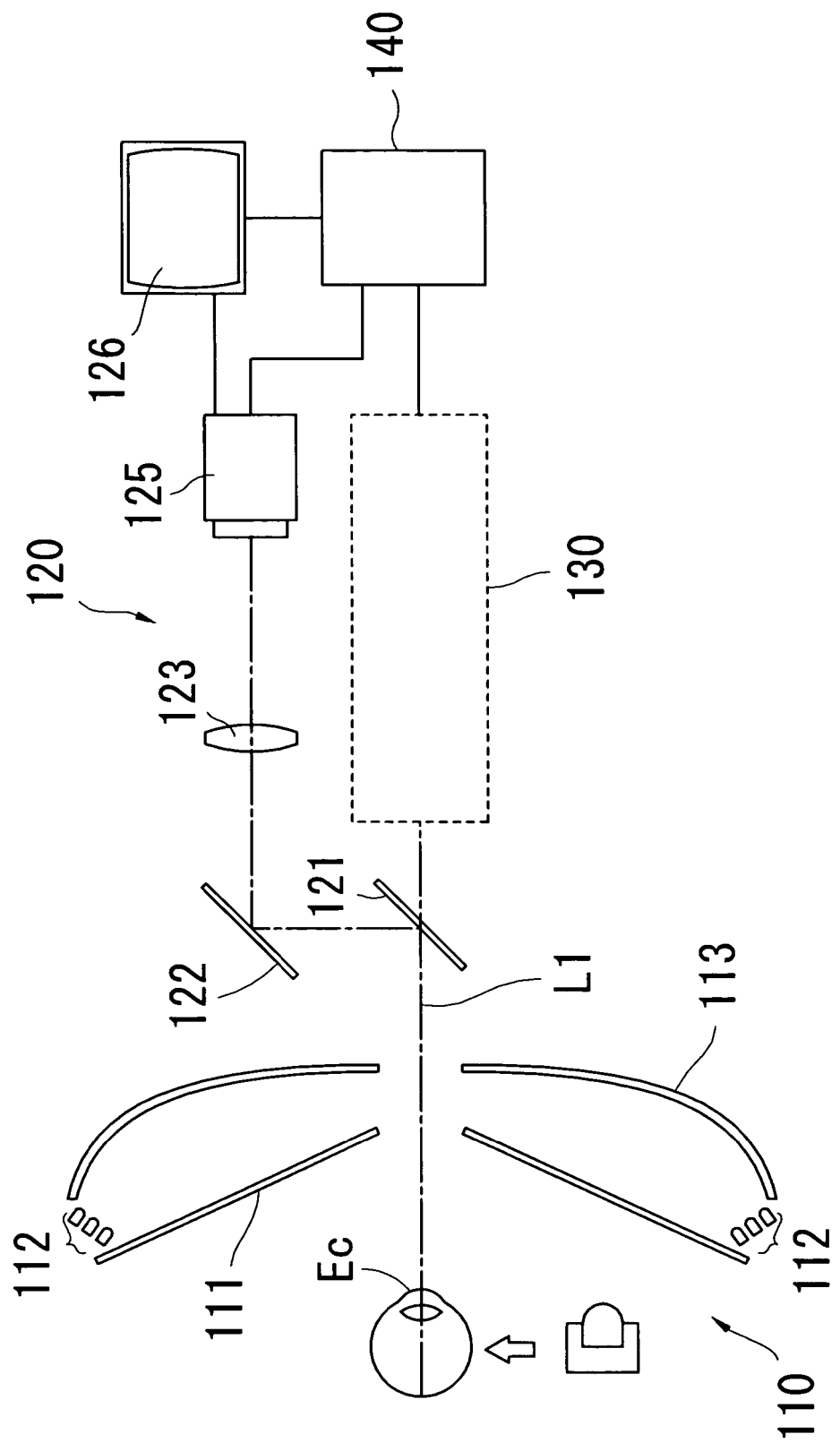
FIG. 4 is a view showing a schematic configuration of a corneal shape measurement apparatus.

FIG. 4 is a view showing a schematic configuration of the measurement apparatus 100. A corneal shape measurement optical system is provided with a measurement index projecting optical system 110 and an index detecting optical system 120. The projecting optical system 110 includes a conic placido plate 111 having an opening in its center, a plurality of illumination light sources 112 such as LED, and a reflecting plate 113. On the placido plate 111, there is a ring pattern in a form of concentric circles with the center on a measurement optical axis L1, and the ring pattern is constituted of a multitude of light transmitting portions and light shielding portions. The illumination light emitted from the light sources 112 is reflected by the reflecting plate 113, and illuminates the placido plate 112 approximately uniformly from the rear of the plate 112. The light having passed through the light transmitting portions of the placido plate 111 comes in a ring pattern and is projected onto the cornea Ec. When the curved surface shape of the reference object 10 is to be measured, the reference object 10 instead of the patient's eye is placed in a predetermined position.

The detecting optical system 120 is provided with a beam splitter 121, a mirror 122, a photographing lens 123, and a CCD camera 125. The reflected light in the ring pattern, which has been projected by the projecting optical system 110, is reflected by the beam splitter 121 and the mirror 122, and then passes through the lens 123 to form an image on a surface of an imaging element of the camera 125. In addition, the detecting optical system 120 doubles as an observation optical system. An anterior eye segment of the patient's eye is illuminated by a light source (not illustrated) designed for illuminating an anterior eye segment. Then, an image of the anterior eye segment is formed on the surface of the imaging element of the camera 125, and is displayed on a TV monitor 126.

Placed behind the beam splitter 121 is a refractive power measurement optical system 130 for measuring a distribution of eye refractive power of the patient's eye. The refractive power measurement optical system 130 includes an optical system for projecting slit light with which scanning is performed by a rotation sector onto a fundus of the patient's eye and a light receiving optical system having plural pairs of photo-detectors. In this system, the photo-detectors are placed at positions approximately conjugate with the cornea Ec in a meridian direction conforming to a scanning direction, and they are arranged in pairs at diametrically opposed positions in relative to the measurement optical axis L1. The slit light and the photo-detectors are rotated synchronously about the optical axis. Based on phase difference signals from each pair of the photo-detectors, the refractive power distribution, which varies in accordance with each meridian direction, is obtained. For more details of the measurement of the eye refractive power distribution, Japanese Patent Application Unexamined Publication Nos. Hei 10-108837 (U.S. Pat. No. 5,907,388) and Hei 11-342152 (U.S. Pat. No. 6,033,075) should be referred to.

The camera 125 and the photo-detectors included in the refractive power measurement optical system 130 output to a calculation/control part 140. The calculation/control part 140 conducts image processing on an image photographed by the camera 125 to detect an edge of a placido-ring image. The calculation/control part 140 determines (calculates) a corneal curvature by obtaining each position of the edge in relative to a corneal center at each step of a predetermined angle (e.g. 1 degree) The same processing is conducted to obtain the curved surface shape of the reference object 10. The surface shapes of the cornea Ec and the reference object 10 obtained by the calculation/control part 140 are displayed in color in topographic form on the TV monitor 126. The eye refractive power distribution obtained by the calculation/control part 140 is also displayed as a color map on the TV monitor 126.

A description will now be given to a method for evaluation of ablation conditions and calibration in the above-described system.

Figure 5A:
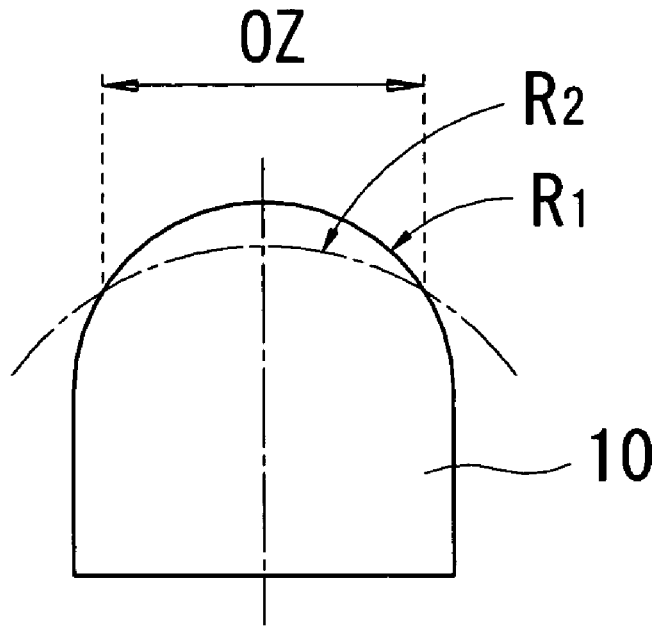
FIGS. 5A and 5B are views illustrating three phases of a curved surface shape of a reference object, a first phase showing a curve before laser irradiation, a second phase showing a curve intended to be formed (attained) by the laser irradiation, and a third phase showing a curve actually formed by the laser irradiation.
Figure 5B:
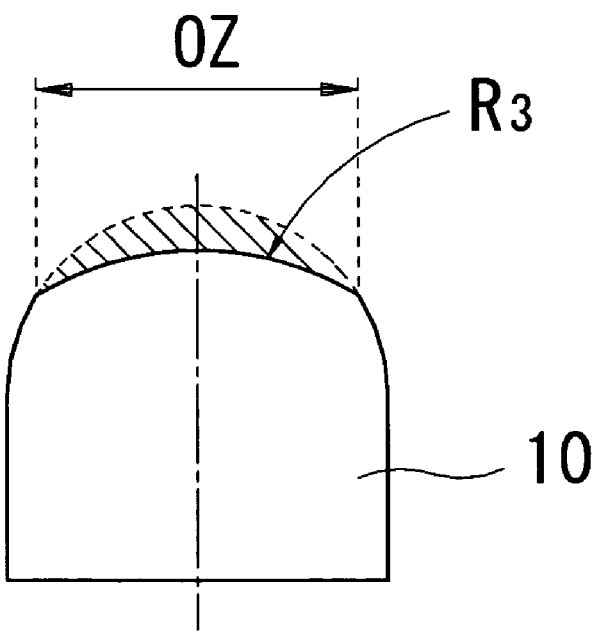

First, the reference object 10 is placed at a predetermined position with respect to the irradiating optical system in the irradiation apparatus 200. The computer 209 included in the irradiation apparatus 200 is used to input dioptric data for correction by a certain amount of a lens. For example, data for removing +3.00 D lens are inputted for myopic correction of −3.00 D. In addition, as shown in FIG. 5A, data about a curved surface shape R1 of the reference object 10 (having a radius of curvature of 7.8 mm) and data about a size of an ablation zone OZ are also inputted. If the curved surface shape R1 of the reference object 10 before laser irradiation (ablation) is unknown, the measurement apparatus 100 is used to find out the shape R1. The computer 209 determines (computes) a curved surface shape R2 intended (expected) to be formed (attained) by the laser irradiation (the ablation) based on those data and a refractive index (known) of the reference object 10. Then, the ablation data for the ablation zone OZ is obtained from the curved surface shapes R1 and R2. Control data for each of the driving parts, which represent laser irradiation conditions, are determined based on the ablation data thus obtained.

The control part 250 controls the opening diameter of the circular aperture 218 and the movement of the mirror 213 based on the control data in the same manner as the above-described myopic correction, so that the central part of the reference object 10 is ablated more deeply than its peripheral part.

After the laser irradiation, the measurement apparatus 100 is used to measure a curved surface shape R3 of the reference object 10 which has actually been ablated (see FIG. 3B). At the time of measurement, the reference object 10 is attached to a chin rest included in the measurement apparatus 100, and is fixed thereto using a jig. In the measurement apparatus 100, as in the case of measuring the cornea Ec, a multitude of the annular placido rings are projected onto the ablated surface of the reference object 10, and their images are detected to measure the curved surface shape R3 having actually been formed by the laser irradiation.

When the ablation conditions are to be evaluated, data about the curved surface shapes R1, R2 and R3 are inputted to the analyzing part 31. The analyzing part 31 determines (analyzes) a discrepancy between the second curved surface shape and the third curved surface shape. For example, the analyzing part 31 compares the curved surface shapes R2 and R3 to determine (analyze) the difference between their curvature distributions. Alternatively, it determines (analyzes) the difference between a distribution of ablation depth for transforming the curved surface shape R1 into the curved surface shape R2 and a distribution of ablation depth on the curved surface shape R3 having been formed by the actual ablation. Results of the analysis are displayed as a topographic image on the TV monitor 126. The topographic image may be displayed in color-map form for easy interpretation. When the curved surface shape R2 is intended to be uniform, the topographic image may be expressed as a map obtained by merely converting the curved surface shape R3 into values of refractive power. These analytical results permit evaluating a distribution of discrepancies on the ablated surface or energy distribution in the present conditions of the irradiation apparatus 200, without actually irradiating a laser beam on the cornea Ec. In addition, the analytical results may be used for adjusting the irradiation apparatus 200 and checking its adjusted conditions. Moreover, the result of surgery may be predicted from those analytical results.

Next, a description will now be given to the method for calibrating (correcting) the control over the irradiation apparatus 200. This method includes a calibration method by which the irradiation apparatus 200 is given a feedback about the curved surface shape R3 measured in the measurement apparatus 100 and a method by which the analyzer 30 calibrates (corrects) the ablation data based on the data about the curved surface shape R3 and the like.

In the case of giving the feedback to the irradiation apparatus 200, the data about the curved surface shape R3 measured with the measurement apparatus 100 are inputted to the computer 209. A discrepancy between the second curved surface shape and the third curved surface shape may be determined (analyzed) as a change of the ablation rate. For example, a value of refractive power of a portion of the lens having actually been ablated may be determined from a change of the radius of curvature made when the laser irradiation changes the curved surface shape R1 into the curved surface shape R3, and from the refractive index of the reference object 10. By comparing this value with a value of refractive power determined for the laser irradiation conditions determined to form the curved surface shape R2, the change of ablation rate of the reference object 10 may be known. As a simpler method, the change of the ablation rate may be used to correct data for driving and controlling the irradiation apparatus 200.

Instead of interpreting the change of the ablation rate based on the change of the refractive power, it is possible to determine the ablation rate of the reference object 10 directly. To be more specific, since the change in the curved surface shape formed by the laser irradiation provides information about depth to which the central part has been ablated, the ablation rate of the reference object 10 may be determined based on that information and the laser irradiating conditions determined to form the curved surface shape R2. In other words, the current ablation rate of the central part may be determined by dividing the ablation depth in the central part by the number of shots (the number of scans) determined for the conditions of laser irradiation having actually been performed.

Further, since the information about depth at an arbitrary position is provided, the ablation rate at each position will be determined by dividing the ablation depth at that particular position by the number of shots (the number of scans) given to the same position. Determining the ablation rate specifically at each position makes it possible to correct shortage of ablation on the peripheral part and/or irregularities of the ablated surface.

It should be noted that it has been empirically known that the ablation rate of a human cornea takes on a value double that of PMMA. Accordingly, when a reference object made of PMMA is used, the current ablation rate for a human cornea may be obtained based on the ablation rate of PMMA determined by the above-described analysis, considering a relationship between the ablation rate of PMMA and that of the cornea.

A description will now be given to calibration of the irradiation apparatus 200. When the opening diameter of the aperture 218 may be expressed as a function of the ablation depth, the opening diameter of the aperture 218 at the current ablation rate is determined (calculated). Then, based on results of the calculation, the opening diameter is actually changed. This method is effective even when the ablation rate is to be varied in rotational symmetry within the ablation zone. When the ablation rate is to be varied in linear symmetry, the opening width of the slit aperture 220 may be controlled to adapt to such variation as well.

In addition, even when the opening diameter of the aperture 218 is controlled in the usual manner, the ablation rate to be varied in rotational symmetry may be attained by making variations in the moving speed of the mirror 213 during one scan of the laser beam between the center and the periphery of the ablation zone. That is, if the periphery is ablated deficiently compared with the center, the moving speed of the mirror 213 is decreased as the laser beams move from the center to the periphery, thereby increasing the number of shots on the peripheral part (i.e. prolonging laser irradiation time). This method is effective for treatment by which ablation is performed to a uniform depth with the opening diameter of the aperture 218 kept unchanged (such treatment is called PTK).

Further, when the ablation rate is to be varied partially, the dividing aperture plate 260 for partial ablation may be controlled to adapt to such variation. The dividing aperture plate 260 is controlled to form the laser beam into small spots, so that part of the laser beam is applied to a region that cannot be treated by controlling the aperture diameter or the movement of the mirror 213 in the above-described manner.

The number of shots (the laser irradiation time) for each position is determined by dividing the ablation depth by the ablation rate.

After the control data for the driving parts are fully corrected using the computer 209 as described above, laser irradiation is performed again on another reference object 10, and its curved surface shape is measured with the measurement apparatus 100 to check a result of the calibration.

Figure 6:
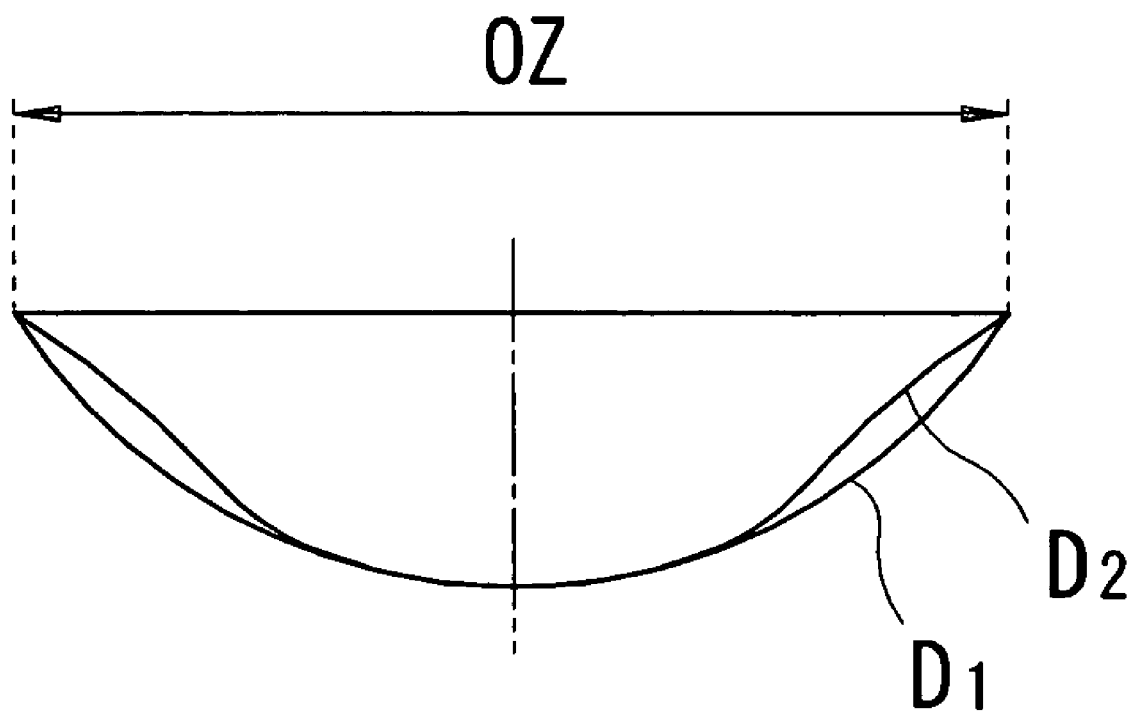
FIG. 6 is a view showing a relationship between an ablation depth intended to be formed (attained) by the laser irradiation and an ablation depth actually formed by the laser irradiation.

Next, a description will now be given to calibration (correction) of the ablation data using the analyzer 30. The data about the ablation zone OZ and the curved surface shapes R1, R2 and R3 are inputted to the analysis part 31, which determines (analyzes) a discrepancy between the second curved surface shape and the third curved surface shape. As shown in FIG. 6, depth D1 (programmed depth) to which the ablation is to be performed at the ablation rate of a reference value is determined (computed) for each position in the ablation zone OZ, based on the data about the curved surface shape R1 before the laser irradiation and the data about the curved surface shape R2 intended (expected) to be formed (attained) by the laser irradiation. Then, depth D2 attained by the actual ablation is determined (computed) for each position in the ablation zone OZ, based on the data about the curved surface shape R1 before the laser irradiation and the data about the curved surface shape R3 formed by the actual ablation. The depths D1 and D2 are used to obtain a correction constant k(r, .), which is a rate of change of the ablation depth at each position, by the following equation:

$$k(r, .) = \text{programmed depth } D1/\text{depth } D2$$

where r is a distance from a center of irradiation, . is an angle with a reference direction, and a positional parameter is expressed as a polar coordinates system (r, .). The correction constant k(r, .) is used to correct the ablation data which is to be inputted to the irradiation apparatus 200 at the time of surgery.

To determine ablation data for actual surgery on a patient's eye, the data about the preoperative corneal surface shape R1 and the data about the preoperative refractive power distribution, both having been measured with the measurement apparatus 200, are inputted to the analyzing part 31. In addition, data about a size of the ablation zone are also inputted. Based on those inputted data, the analysis part 31 determines (analyzes) the ablation data (shot data) for the ablation rate set at the reference value. The data about a wide range of the refractive power distribution is used to determine ablation data by which aberration of the eye can be corrected as well (regarding this calculation, see Japanese Patent Application Unexamined Publication No. Hei 11-342152 corresponding to U.S. Pat. No. 6,033,075). Instead of the analysis part 31, the measurement apparatus 200 may be configured to determine the ablation data. The determined ablation data is multiplied by the above-mentioned correction constant k(r, .), thus determining ablation data which are the shot data thus corrected.

The corrected ablation data are inputted to the irradiation apparatus 200. The irradiation apparatus 200 controls the driving parts 214, 216, 219, 221 and 268 based on the ablation data corrected in advance, thereby allowing the ablation to be performed as intended.

Up to this point, the irradiation apparatus 200 has been described as being configured to use the control of apertures and the parallel scanning with laser beams. However, the apparatus 200 may adopt a method using a galvano mirror or the like for providing scans with laser beams formed into small spots of about 1.0 mm.

INDUSTRIAL APPLICABILITY

As described above, according to the present invention, ablation conditions may be evaluated easily through the use of a reference object having a curved surface shape closely analogous to a curved surface shape of a target object. In addition, the target object may be thereby ablated with good accuracy. Further, the present invention offers an economical advantage since it does not require an apparatus dedicated to measuring the curved surface shape of the reference object.

The invention claimed is:

1. A method for performing at least one of an analysis on a state of a surface ablated by a corneal surgery apparatus which ablates a cornea by irradiating a laser beam, an analysis on inconsistency in the laser beam, and calibration on irradiation data of the laser beam, the method comprising:

a step of preparing a reference object for evaluation having a first curved surface shape being approximate to a curved surface shape of the cornea;

an ablation step of setting irradiation conditions of the laser beam of the corneal surgery apparatus so that the first curved surface shape is changed into a second curved surface shape, and irradiating the laser beam onto the reference object by the corneal surgery apparatus under the set irradiation conditions to ablate the reference object;

a measurement step of measuring a third curved surface shape, which has actually been formed on the reference object by the ablation, by a corneal shape measurement optical unit; and an analysis step of analyzing that the third curved surface shape has been formed in an attempt to change the first curved surface shape into the second curved surface shape, and performing at least one of the analysis on the state of the ablated surface, the analysis on the inconsistency in the laser beam, and the calibration on the irradiation data of the laser beam.

2. The method according to claim 1, further comprising a display step of displaying a result of the analysis.

3. The method according to claim 1, wherein the reference object has a known ablation rate relative to an ablation rate of the cornea.

* * * * *